United States Patent [19]

Miyajima et al.

[11] Patent Number: 4,983,593
[45] Date of Patent: Jan. 8, 1991

[54] PHARMACEUTICAL COMPOSITION OF DIHYDROPYRIDINE COMPOUND

[75] Inventors: Masaharu Miyajima; Yukiya Yamaguchi, both of Konan; Takao Tsunematsu; Toshihisa Oda, both of Shiraoka, all of Japan

[73] Assignees: Zeria Pharmaceutical Co; Nissan Chemical Industries Ltd., both of Tokyo, Japan

[21] Appl. No.: 358,144

[22] Filed: May 30, 1989

[30] Foreign Application Priority Data

May 30, 1988 [JP] Japan ................................. 63-132262
Mar. 2, 1989 [JP] Japan ..................................... 1-50471

[51] Int. Cl.$^5$ ............................................. A61R 31/66
[52] U.S. Cl. ....................................................... 514/110
[58] Field of Search ......................................... 514/110

[56] References Cited

FOREIGN PATENT DOCUMENTS 230944 5/1987 European Pat. Off. .
231026 5/1987 European Pat. Off. .
62-123117 6/1987 Japan .

OTHER PUBLICATIONS

Chemical and Pharmaceutical Bulletin, vol. 35, No. 9, Sep. 1987, pp. 3935–3939, Pharmaceutical Society of Japan, Tokyo, JP; N. Ohnishi et al.

*Primary Examiner*—Allen J. Robinson
*Attorney, Agent, or Firm*—Oblon, Spivak, McClelland, Maier & Neustadt

[57] ABSTRACT

A pharmaceutical composition comprising: a 1:1 solvate of 5-(5,5-dimethyl-1,3,2-dioxaphosphorinane-2-yl)-1,4-dihydro-2,6-dimethyl-4-(3- itrophenyl)-3-pyridine carboxylic acid 2-(phenylmethyl)amino) ethyl ester P-oxide hydrochloride-thanol (NZ-105) and hydroxypropylmethylcellulose acetate succinate is disclosed. the composition can easily be prepared into tablets, capsules, granules, and powders, which exhibit an enhanced bioavailability, e.g. provides a high blood concentration of the active component NZ-105 and ensures a high total drug absorption.

4 Claims, No Drawings

PHARMACEUTICAL COMPOSITION OF DIHYDROPYRIDINE COMPOUND

BACKGROUND OF THE INVENTION

1. Field of the Invention

This invention relates to a pharmaceutical composition comprising a 1:1 solvate of 5-(5,5-dimethyl-1,3,2-dioxaphosphorinane-2-yl)-1,4-dihydro-2,6-dimethyl-4-(3-nitrophenyl)-3-pyridine carboxylic acid 2-(phenyl(phenylmethyl)amino) ethyl ester P-oxide hydrochlorideethanol (such a solvate is herein abbreviated as "NZ-105") possessing hypotensive activity.

2. Description of the Background

The effective pharmaceutical component, NZ-105, of the composition of this invention is a derivative of 1,4-dihydropyridine-5-phosphonic acid and has the following chemical formula:

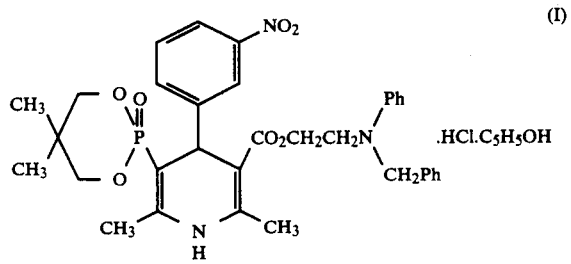

wherein Ph represents a phenyl group. This is a novel compound possessing vasodilative and hypotensive activity on account of its calcium antagonistic activity and useful as a cardiovascular drug.

Nicardipine and nifedipine are well known as 1,4-dihydropyridine-type compounds. Because of very poor solubility in water, these compounds can not be absorbed through gastrointestinal tracts in a sufficient amount. Improvement in the solubility of these compounds has thus been desired in view of the promotion of their bioavailability. Various methods have been proposed to improve solubility of these compounds, including dissolving these compounds into an organic solvent, pulverizing the compounds, utilizing multi-crystal forms, formulating a surface active agent or a polymeric compound, etc. Japanese Patent Publication No. 48810/1984, for example, proposes converting nicardipine hydrochloride into an amorphous type. Japanese Patent Laid-open No. 123117/1987 discloses formulating an organic acid and a water soluble polymer to nicardipine hydrochloride to promote its solubility. Methylcellulose, hydroxypropylcellulose, hydroxypropylmethylcellulose, or a mixture of these compounds are used as water soluble polymeric compounds. Other polymeric compounds are polyvinylpyrrolidone, methacrylic acid-methylacrylate copolymer, carboxymethylethylcellulose, hydroxypropylmethylcellulose phthalate, cellulose phthalate acetate, and the like.

Based on this technological background, the present inventors have studied the possibility of promoting the bioavailability of NZ-105 by pulverizing its crystals. This method, however, did not result in an improvement in the solubility of NZ-105 of a degree to promote its bioavailability.

Formulating a polymeric compound to NZ-105 was also studied. None of the above-mentioned polymers which have been proposed for use in conjunction with 1,4-dihydropyridine-type compounds gave a satisfactory improvement in the promotion of the solubility of NZ-105. Besides, the formulation of such a polymer as polyvinylpyrrolidone, hydroxypropylcellulose, or hydroxypropylmethylcellulose into a preparation of NZ-105 required the use of a larger amount of a disintegrator in the tablet to ensure disintegration of the tablet in digestive organs resisting the binding force of these polymeric compounds. This entailed larger size tablets. Other polymeric compounds, such as hydroxypropylmethylcellulose phthalate, cellulose acetate phthalate, methacrylic acid-methylmethacrylate copolymer, polyvinylacetaldiethylaminoacetate, and the like, required the use of a relatively large amount of these compounds to be formulated in order to improve the solubility of NZ-105 and to promote its bioavailability. This also entailed larger size tablets.

A need has therefore existed for a stable composition of an NZ-105 preparation possessing a sufficient bioavailability and easily prepared into tablets, capsules, granules, powders, etc.

The present inventors have conducted further studies in order to resolve the above-mentioned problems and found that by formulating hydroxypropylmethylcellulose acetate succinate (hereinafter abbreviated as "HPMCAS") into NZ-105 a composition having a remarkably enhanced bioavailability and easily prepared into tablets, capsules, granules, powders, and the like could be obtained. Such a finding has led to the completion of the present invention.

SUMMARY OF THE INVENTION

Accordingly, an object of the present invention is to provide a composition comprising NZ-105 and HPMCAS.

Another object of the present invention is to provide a process for preparing said composition which comprises dissolving NZ-105 and HPMCAS into an organic solvent and removing the solvent by evaporation.

Other objects, features and advantages of the invention will hereinafter become more readily apparent from the following description.

DETAILED DESCRIPTION OF THE INVENTION AND PREFERRED EMBODIMENTS

NZ-105 which is the active pharmaceutical component of the composition of this invention can be prepared, for example, according to the following process:

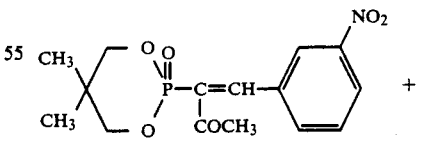

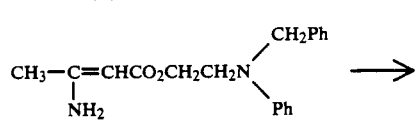

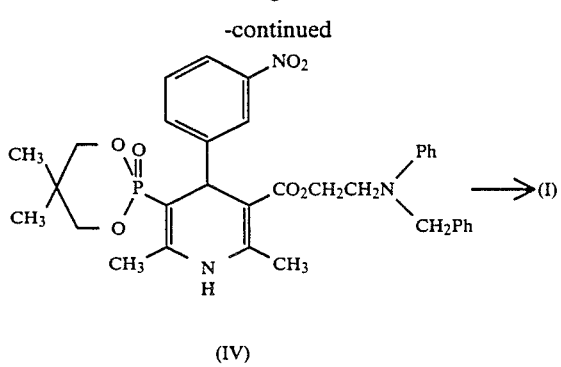

in which Ph have the meaning as previously defined.

Specifically, the process for producing NZ-105 (I) comprises the reaction of α-(3-nitrobenzylidene)-acetonylphosphonic acid 2,2-dimethylpropylene ester (II) and 3-aminocrotonic acid 2-(N-benzyl-N-phenyl-)aminoethyl ester (III) in an inert solvent to produce 5-(5,5-dimethyl-1,3,2-dioxaphosphorinane-2-yl)-1,4-dihydro-2,6-dimethyl-4-(3-nitrophenyl)-3-pyridinecarboxylic acid 2-(phenyl-(phenylmethyl)amino) ethyl ester P-oxide (IV) or its solvate, followed by treatment of the compound (IV) or its solvate with hydrochlic acid and ethanol.

Inert solvents which can be used in the above reaction may be an alcohol, e.g. methanol, ethanol, propanol, isopropanol, etc., an ether, e.g. 1,2-dimethoxyethane, THF, etc., an aromatic hydrocarbon, e.g. benzene, toluene, xylene, etc., a nitrile, e.g. acetonitrile, benzonitrile, etc., an amide, e.g. DAM, DMF, N-methylpyrrolidone, etc., a sulfoxide, e.g. DMSO, sulfolane, etc., an ester, e.g. ethyl acetate, butyrolactone, etc., pyridine, or the like.

The reaction can be carried out at room temperature to 200° C., preferably at 60°-140° C., for 1-100 hours, preferably for 5-20 hours.

After the completion of the reaction, NZ-105 (I) can be obtained by treating the compound (IV) or its solvate with ethanol and hydrochloric acid.

HPMCAS used in this invention is an acetic acid and succinic acid ester mixture of hydroxypropylmethylcellulose. An example of this mixture which can be given is "Shinetsu AQOAT" (Trade name, manufactured by Shinetsu Chemical Industries Co., Ltd.). A preferable range for the residual group composition in HPMCAS used in this invention, in terms of an average value (succinoyl DS value) of hydroxy group number substituted by succinoyl group per glucose residue in cellulose, is 0.1-0.4. Further, it is desirable that a ratio of succinoyl DS value and acetyl DS value (succinoyl DS value/acetyl DS value) be in a range of 0.1-0.8, especially of 0.5-0.8.

An NZ-105 composition of this invention can be prepared by dissolving NZ-105 and HPMCAS in an organic solvent, removing the solvent by means of vacuum-drying, spray-drying, freeze-drying, or the like to produce powder or particles of NZ-105 and HPMCAS. Alternatively, with the use of a filler particle as a core, NZ-105 and HPMCAS can be spray coated by means of a fluidized bed granulation method, a centrifugal coating method, or pan coating method to produce granules. The granules can also be prepared by adding a solvent to a filler and kneading the mixture, followed by drying.

An alcohol, e.g. methanol, ethanol, isopropanol, etc., acetone, methylene chloride, or the like can be used as a solvent for dissolving NZ-105 and HPMCAS. An example of a preferable solvent is a mixture of an alcohol such as ethanol or isopropanol and methylene chloride, with an alcohol/methylene chloride ratio of 1/0.4 to 1/5, especially of 1/0.7 to 1/1.5 by volume.

A desirable result can be obtained by formulating an amount of 1-7 parts by weight, especially 3-5 parts by weight of HPMCAS per unit weight of NZ-105.

When the preparation of this invention is spray coated, either water soluble or insoluble filler, including crystalline lactose, granulous sugar, crystalline cellulose, calcium hydrogen phosphate anhydride, and the like, can be used as a core. Such a core material has a particle size normally of 100-400 mesh, and preferably of 150-300 mesh.

The composition of this invention thus prepared can be used in a form of powder or granule, as they are or mixed with fillers. It can also be made into tablets, capsules, or pills together with disintegrats, binders, lubricants, or other additives commonly used in the preparation of drugs.

Examples of fillers which can be used include sugars, e.g. lactose, sucrose, etc., glycitols, e.g. mannitol, sorbitol, xylitol, etc., starches, e.g. corn starch, potato starch, wheat starch, rice starch, etc., crystalline cellulose, inorganic salts, e.g. calcium hydrogen phosphate anhydride, synthetic aluminum silicate, etc., and the like.

Given as examples of disintegrators which can be used are starches, e.g. corn starch, potato starch, wheat starch, rice starch, etc., hydroxypropyl starch, calcium salt of carboxymethylcellulose, cross-linked sodium salt of carboxymethylcellulose, cross-linked polyvinylpyrrolidone, low-substituted hydroxypropylcellulose, and the like. The use of 2-15% by weight, especially 3-10% by weight, of disintegrats for the total weight of the composition is preferable, when the composition is formed into tablets or capsules.

Binders which can be used include, for example, starches, e.g. corn starch, potato starch, wheat starch, rice starch, etc., gelatinized starches, partially pregelatinized starches, dextrin, sugars such as purified sugar, sodium carboxymethylcellulose, methylcellulose, ethylcellulose, hydroxypropylcellulose, polyvinylpyrrolidone, and the like.

Examples of lubricant which can be used are talc, waxes, stearic acid, magnesium stearate, light anhydrous silicic acid, and the like.

In addition to the above-mentioned components, formulating such compounds as urea, surface active agents, and the like is desirable when the composition is prepared into a pharmaceutical preparation.

Other features of the invention will become apparent in the course of the following description of the exemplary embodiments which are given for illustration of the invention and are not intended to be limiting thereof.

EXAMPLES

Reference Example 1

(1) 13 g of α-(3-nitrobenzylidene)-acetnilphosphonic acid 2,2-dimethylpropylene ester (II) and 11.9 g of 3-aminocrotonic acid 2-(N-benzyl-N-phenyl)aminoethyl ester (III) were mixed with 100 g of toluene and the mixture was refluxed for 2 hours while removing water produced in the reaction by azeotropic dehydration. 23.6 g of yellow crystals of one-mole toluene solvate of 5-(5,5-dimethyl-1,3,2-dioxaphosphorinane-2-yl)-1,4- dihydro-2,6-dimethyl-4-(3-nitrophenyl)-3-pyridinecarboxylic acid 2-(phenyl(phenylmethyl)amino) ethyl ester P-oxide (IV) was obtained by cooling the reaction mixture to room temperature (yield: 85%).

The crystals were recrystallized in ethyl acetate to produce a compound without a solvent incorporated therein. This last produced compound had a melting point and an NMR spectrum described below. m.p. 156°–158° C.

NMR (CDCl$_3$) δ:0.66 (3H, s), 0.99 (3H, s), 2.25 (3H, s), 2.3 (3H, d, J=2.5Hz), 3.5–3.7 (4H, m), 4.1–4.4 (4H, m), 4.51 (2H, s), 4.9 (1H, d, J=10.9Hz), 6.47 (1H, d, J=4.2Hz), 6.67 (3H, m), 7.1–7.35 (8H, m), 7.58 (1H, d, J=6.6Hz), 7.96 (1H, m), 8.07 (1H, t, J=1.9Hz).

(2) 193.1 g of the toluene solvate (IV) prepared in (1) above was dissolved into 996 g of ethanol under heating. 51 g of 21% hydrochloric acid-ethanol was added to the solution and the mixture was cooled to room temperature to produce 185.2 g of hydrochloride of 1 mol ethanol solvate of compound (IV) which is the target compound NZ-105, as yellow crystals (yield 97.2%).

m.p. 149°–155° C. (decomposed).

Example 1

60 g of NZ-105, 180 g of HPMCAS, and 30 g of urea were dissolved into 3 liter of an ethanol-methylene chloride (1/1 by volume) mixed solvent. The solution was sprayed onto 120 g of calcium hydrogen phosphate anhydride using a fluidized bed granulation apparatus and dried to obtain granules. 130 g of the granules were mixed and thoroughly blended with 23.6 g of crystalline cellulose, 12 g of cross-linked polyvinylpyrrolidone, 0.4 g of light anhydrous silicic acid, and 1 g of magnesium stearate. The mixture was press molded to produce tablets each containing 20 mg of NZ-105 and having a 7.5 mm diameter and weighing 167 mg.

Example 2

40 g of NZ-105, 120 g of HPMCAS (Shinetsu AQOAT, LG-type; manufactured by Shinetsu Chemical Industries Co., Ltd.), and 20 g of urea were dissolved into 2 liter of an ethanol-methylene chloride (1/1 by volume) mixed solvent. The solution was sprayed onto 200 g of calcium hydrogen phosphate anhydride using a fluidized bed granulation apparatus and dried to obtain granules. 95 g of the granules thus prepared were mixed and thoroughly blended with 19 g of crystalline cellulose, 10 g of carboxymethylcellulose calcium, and 1 g of magnesium stearate. The mixture was press molded to produce tablets each containing 20 mg of NZ-105 and having a 9 mm diameter and weighing 250 mg.

Example 3

50 g of NZ-105, 150 g of HPMCAS (Shinetsu AQOAT, LF-type; manufactured by Shinetsu Chemical Industries Co., Ltd.) and 25 g of urea were dissolved into 3 liter of an ethanol-methylene chloride (1/1 by volume) mixed solvent. The solution was sprayed onto 800 g of crystalline latose using a fluidized bed granulation apparatus and dried to obtain granules. The granules thus prepared were screened through a #12 sieve (openings: 1,400 μm) and a #42 sieve (openings: 355 μm) to obtain granules having particle size of 1,400–355 μm. The granules contained 20 mg of NZ-105 per 410 mg.

Example 4

50 g of NZ-105, 150 g of HPMCAS (Shinetsu AQOAT, LF-type; manufactured by Shinetsu Chemical Industries Co., Ltd.) and 25 g of urea were dissolved into 3 liter of an ethanol-methylene chloride (1/1 by volume) mixed solvent. The solution was sprayed onto 200 g of calcium hydrogen phosphate anhydride using a fluidized bed granulation apparatus and dried to obtain granules. 85 g of the granules thus prepared were mixed and thoroughly blended with 40 g of crystalline cellulose and 10 g of carboxymethylcellulose calcium, and the mixture was filled into No. 1 capsules, 270 mg per capsule, to produce capsules each containing 20 mg of NZ-105.

Example 5

50 g of NZ-105, 250 g of HPMCAS (Shinetsu AQOAT, LF-type; manufactured by Shinetsu Chemical Industries Co., Ltd.) and 25 g of urea were dissolved into 3 liter of an ethanol-methylene chloride (1/1 by volume) mixed solvent. The solution was sprayed onto 250 g of calcium hydrogen phosphate anhydride using a fluidized bed granulation apparatus and dried to obtain granules. 105 g of the granules thus prepared were mixed and thoroughly blended with 35 g of crystalline cellulose and 15 g carboxymethylcellulose calcium, and the mixture was filled into No. 1 capsules, 310 mg per capsule, to produce capsules each containing 20 mg of NZ-105.

Example 6

4 g of NZ-105 and 12 g of HPMCAS (Shinetsu AQOAT, LF-type; manufactured by Shinetsu Chemical Industries Co., Ltd.) were dissolved into 100 ml of an ethanol-methylene chloride (¼ by volume) mixed solvent. 30 g of lactose was added to and thoroughly dispersed into the solution. The liquid thus prepared was dried in vacuo. The dried material was pulverized to produce a powdery material. 10.7 g of corn starch and 0.3 g of talc were added to 23 g of the powdery material. The mixture was well blended and filled into No. 1 capsules, 340 mg per capsule, to produce capsules each containing 20 mg of NZ-105.

Comparative Example 1

4 g of NZ-105 and 12 g of hydroxypropylmethylcellulose 2910 (TC-5 E type; manufactured by Shinetsu Chemical Industries Co., Ltd.) were dissolved into 100 ml of an ethanol-methylene chloride (¼ by volume) mixed solvent. 30 g of lactose was added to and thoroughly dispersed into the solution. The liquid thus prepared was dried in vacuo. The dried material was pulverized into powder. 10.7 g of corn starch and 0.3 g of talc were added to 23 g of the powder. The mixture was well blended and filled into No. 0 capsules, 340 mg per capsule, to produce capsules each containing 20 mg of NZ-105.

Comparative Example 2

4 g of NZ-105 and 12 g of hydroxypropylmethylcellulose phthalate (HPMCP, HP-55 type; manufactured by Shinetsu Chemical Industries Co., Ltd.) were dissolved into 100 ml of an ethanol-methylene chloride (¼ by volume) mixed solvent. 30 g of lactose was added to and thoroughly dispersed into the solution. The liquid thus prepared was dried in vacuo. The dried material was pulverized into powder. Capsules each containing 20 mg of NZ-105 were prepared in the same manner as Comparative Example 1 using this powdery material.

Comparative Example 3

4 g of NZ-105 and 12 g of methacrylic acid-methyl methacrylate copolymer (Euydragit L-type, manufactured by Rohm and Haas Co.) were dissolved into 100 ml of an ethanol-methylene chloride (¼ by volume) mixed solvent. 30 g of lactose was added to and thoroughly dispersed into the solution. The liquid thus prepared was dried in vacuo. The dried material was pulverized to produce powder. Capsules each containing 20 mg of NZ-105 were prepared in the same manner as Comparative Example 1 using the powder.

Comparative Example 4

4 g of NZ-105 and 12 g of polyvinylacetaldiethylamino acetate (AEA, manufactured by Sankyo Co., Ltd.) were dissolved into 100 ml of an ethanol-methylene chloride (¼ by volume) mixed solvent. 30 g of lactose was added to and thoroughly dispersed into the solution. The liquid thus prepared was dried in vacuo. The dried material was pulverized to produce a powdery material. Capsules each containing 20 mg of NZ-105 were prepared in the same manner as Comparative Example 1 using this powdery material.

Comparative Example 5

50 g of NZ-105, 150 g of polyvinylacetaldiethylamino acetate (AEA, manufactured by Sankyo Co., Ltd.), and 25 g of urea were dissolved into 3 liter of an ethanol-methylene chloride (¼ by volume) mixed solvent. The solution was sprayed onto 300 g of calcium hydrogen phosphate anhydride using a fluidized bed granulation apparatus and dried to obtain granules. 105 g of the granules were mixed and blended thoroughly with 75 g of crystalline cellulose calsium, 20 g of carboxymethylcellulose. The mixture was filled into No. 0 capsules, 400 mg per capsule, to produce capsules each containing 20 mg of NZ-105.

Comparative Example 6

20 g of NZ-105 pulverized to an average size of 6 μm, 210 g of lactose, 100 g of corn starch, and 10 g of carboxymethylcellulose calcium were mixed and thoroughly blended. The blend was filled into No. 0 capsules, 340 mg per capsule, to produce capsules each containing 20 mg of NZ-105.

Test Example 1

Dissolution Test

A dissolution test was conducted on the preparations prepared in Example 6 and Comparative Examples 1–4 (each containing 20 mg of NZ-105) according to the following conditions:

Test Method: Dissolution test of Japanese Pharmacopeia, 11th Revision (Paddle Method).

Test Fluid: Japanese Pharmacopeia first fluid (Comparative Example 4) and Japanese Pharmacopeia second fluid (Example 6, Comparative Example 1–3), 500 ml.

Temperature: 37±0.5° C.

Stirring: 100 rpm.

Quantitative Analysis: Test solutions were filtered through a millipore filter (0.2 μm). The filtrate was diluted with methanol to a 2-fold volume, followed by measurement of the absorbance at 330 nm.

The results are shown in Table 1.

TABLE 1

| Tested Preparations | Dissolution (μg/ml) | | | | | |
|---|---|---|---|---|---|---|
| | 5 min | 10 min | 15 min | 20 min | 25 min | 30 min |
| Example 6 | 22.2 | 32.5 | 32.2 | 30.3 | 29.8 | 30.0 |
| Comparative Example 1 | 2.1 | 2.1 | 1.8 | 1.9 | 1.2 | 1.5 |
| Comparative Example 2 | 12.6 | 13.0 | 10.7 | 9.8 | 7.0 | 4.2 |
| Comparative Example 3 | 9.7 | 15.1 | 13.9 | 15.0 | 15.4 | 16.2 |
| Comparative Example 4 | 2.2 | 11.3 | 15.7 | 17.0 | 17.8 | 17.8 |

The capsule of Comparative Example 4 was tested using Japanese Pharmacopeia first fluid (pH 1.2), since this capsule contained polyvinylacetaldiethylamino acetate which is a polymeric compound dissolvable at an acidic pH value.

Table 1 demonstrates that the capsule of Example 6 exhibits higher dissolution than the capsules of Comparative Examples 1–4 using polymeric compounds other than HPMCAS. The capsule of Comparative Example 1 using hydroxypropylmethylcellulose 2910 which is a water soluble polymer dissolved very little throughout the test period. In the test using the capsule of Comparative Example 2 containing hydroxypropylmethylcellulose phthalate which is the pH dependent, alkali soluble-type polymeric compound as HPMCAS, recrystallization of NZ-105 took place 10 minutes after start of the test and the dissolution began to decline. The capsule of Comparative Example 3 containing methacrylic acid-methyl methacrylate copolymer, which is pH dependent, alkali soluble-type polymer, and the capsule of Comparative Example 4 containing polyvinylacetaldiethylamino acetate, which is also pH dependent, acidic soluble-type polymers, although did not recrystallize NZ-105, exhibited dissolutions about ½ of that of the capsule using HPMCAS, evidencing that they are undesirable in view of practical bioavailability.

Test Example 2

Blood Concentration

The preparations prepared in Examples 1–5 and Comparative Examples 5 and 6, each containing 20 mg of NZ-105, were orally administered to Beagle dogs (weight: about 10 kg) which were fasted overnight. Blood was collected from each dog 0.5, 1, 2, 3, 4, and 6 hours after the administration. The measurement of the blood concentration of NZ-105 was carried out by means of HPLC on NZ-105 extract samples from plasma. The blood concentrations and their parameters are shown in Table 2.

TABLE 2

| Tested Preparations | Blood Concentrations (ng/ml) | | | | | | Parameters | | |
|---|---|---|---|---|---|---|---|---|---|
| | 0.5 | 1 | 2 | 3 | 4 | 6 (hrs) | Cmax | Tmax | AUC |
| Example 1 | 71.1 | 48.0 | 23.4 | 16.3 | 11.1 | 8.3 | 71.1 | 0.5 | 153.0 |
| Example 2 | 22.6 | 30.7 | 17.9 | 10.2 | 5.3 | 0.0 | 30.7 | 1.0 | 78.1 |
| Example 3 | 35.4 | 72.5 | 29.9 | 13.4 | 5.9 | 0.0 | 72.5 | 1.0 | 134.0 |
| Example 4 | 8.4 | 54.5 | 52.1 | 19.9 | 7.4 | 0.0 | 54.5 | 1.0 | 141.8 |

TABLE 2-continued

| Tested | Blood Concentrations (ng/ml) | | | | | | Parameters | | |
|---|---|---|---|---|---|---|---|---|---|
| Preparations | 0.5 | 1 | 2 | 3 | 4 | 6 (hrs) | Cmax | Tmax | AUC |
| Example 5 | 0.0 | 41.4 | 87.2 | 43.5 | 21.5 | 8.7 | 87.2 | 2.0 | 211.5 |
| Comparative Example 5 | 0.0 | 0.0 | 14.5 | 14.9 | 6.4 | 0.0 | 14.9 | 3.0 | 49.7 |
| Comparative Example 6 | 0.0 | 0.0 | 0.0 | 0.0 | 0.0 | 0.0 | 0.0 | 0.0 | 0.0 |

Cmax: Maximum blood concentration (ng/ml)
Tmax: Time required to arrive at the maximum blood concentration (hour)
AUC: The area under the blood concentration-time curve (ng.hour/ml)

The composition of the present invention can provide a high blood concentration of the pharmaceutical component NZ-105 and ensures the high total drug absorption (AUC), and can easily be prepared into pharmaceutical preparations such as capsules, granules, powders, tablets, and the like.

Obviously, numerous modifications and variations of the present invention are possible in light of the above teachings. It is therefore to be understood that within the scope of the appended claims, the invention may be practiced otherwise than as specifically described herein.

What is claimed is:

1. A pharmaceutical composition comprising (i) a 1:1 solvate of 5-(5,5-dimethyl-1,3,2-dioxaphosphorinane-2-yl)-1,4-dihydro-2,6-dimethyl-4-(3-nitrophenyl)-3-pyridine carboxylic acid 2-(phenyl(phenylmethyl)amino) ethyl ester P-oxide hydrochloride-ethanol and (ii) hydroxypropylmethylcellulose acetate succinate, wherein (ii) is present in an amount of 1-7 parts by weight per unit weight (i).

2. A process for preparing a pharmaceutical composition comprising: (i) a 1:1 solvate of 5-(5,5-dimethyl-1,3,2-dioxaphosphorinane-2-yl)-1,4-dihydro-2,6-dimethyl-4-(3-nitrophenyl)-3-pyridine carboxylic acid 2-(phenyl(phenylmethyl)amino) ethyl ester P-oxide hydrochloride-ethanol and (ii) hydroxypropylmethyl-cellulose acetate succinate which comprises dissolving (i) a 1:1 solvate of 5-(5,5-dimethyl-1,3,2-dioxaphosphorinane-2-yl)-1,4-dihydro-2,6-dimethyl-4-(3-nitrophenyl)-3-pyridine carboxylic acid 2-(phenyl(phenylmethyl)amino) ethyl ester P-oxide hydrochloride-ethanol and (ii) hydroxypropylmethylcellulose acetate succinate into an organic solvent and removing said organic solvent by evaporation, wherein (ii) is present in an amount of 1-7 parts by weight per unit (i).

3. The pharmaceutical composition according to claim 1, wherein (ii) is present in an amount of 3-5 parts by weight per unit weight (i).

4. The process according to claim 2, wherein (ii) is present in an amount of 3-5 parts by weight per unit weight (i).

* * * * *